United States Patent
Stearns et al.

[19]

[11] Patent Number: 5,891,071
[45] Date of Patent: Apr. 6, 1999

[54] LEG BRACE

[75] Inventors: Jeffrey Stearns, New York, N.Y.; Juan Bautista Paez, Darnestown, Md.

[73] Assignee: Lenox Hill, a Division fo Dobi-Symplex, Bethesda, Md.

[21] Appl. No.: 577,835

[22] Filed: Dec. 22, 1995

Related U.S. Application Data

[60] Provisional application No. 60/008,343 Dec. 7, 1995.
[51] Int. Cl.⁶ .................................................. A61F 5/00
[52] U.S. Cl. ................................................ 602/26; 602/23
[58] Field of Search ............................. 602/5–8, 16, 20, 602/23–26

[56] References Cited

U.S. PATENT DOCUMENTS

| | | |
|---|---|---|
| 4,387,709 | 6/1983 | Shen . |
| 4,732,143 | 3/1988 | Kausek et al. .............................. 602/16 |
| 4,796,610 | 1/1989 | Cromartie .................................. 602/26 |
| 4,854,308 | 8/1989 | Drillio ....................................... 602/16 |
| 4,928,670 | 5/1990 | DeLorenzo . |
| 4,940,044 | 7/1990 | Castillo ..................................... 602/16 |
| 4,986,264 | 1/1991 | Miller ................................... 602/26 X |
| 5,133,341 | 7/1992 | Singer et al. .......................... 602/26 X |
| 5,336,161 | 8/1994 | Lengyel .................................... 602/26 |
| 5,384,913 | 1/1995 | Hendry ................................. 602/26 X |

*Primary Examiner*—Linda C. Dvorak
*Attorney, Agent, or Firm*—Stroock & Stroock & Lavan LLP

[57] ABSTRACT

A leg brace and method for forming thereof is provided. The brace includes a frame formed of at least a thermoplastic material. A harness is fixed to the frame, the harness being retained adjacent a user's leg during use. The leg brace may be further formed with a tibial restricting portion running along and substantially parallel to the medial shaft of a user's tibia during use, thereby preventing any unwanted movement or rotation of the user's tibia. The brace is formed by forming a brace core of a mixture of a thermoplastic material and a blowing agent and then placing a composite material in contact with the core. Next, the core and composite material are heated in a mold to a temperature sufficient to allow the thermoplastic material to become molten, causing the blowing agent to expand and force the composite material against an interior wall of the mold cavity and to form a thermoplastic cellular core. Next, after cooling, the leg brace is reheated to a temperature sufficient to allow the thermoplastic material to become malleable, but not sufficient to destroy the structural integrity of the leg brace, and then the leg brace is reshaped for a custom fit.

21 Claims, 6 Drawing Sheets

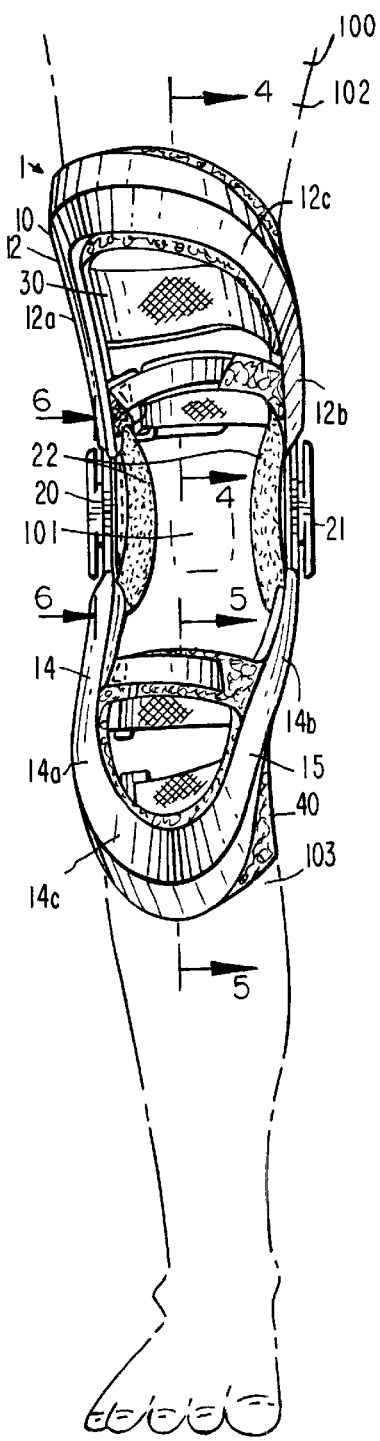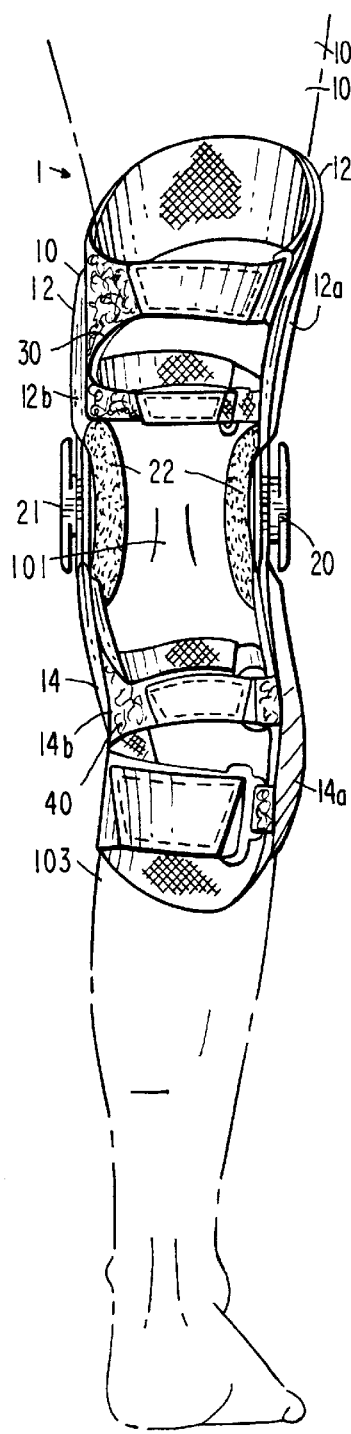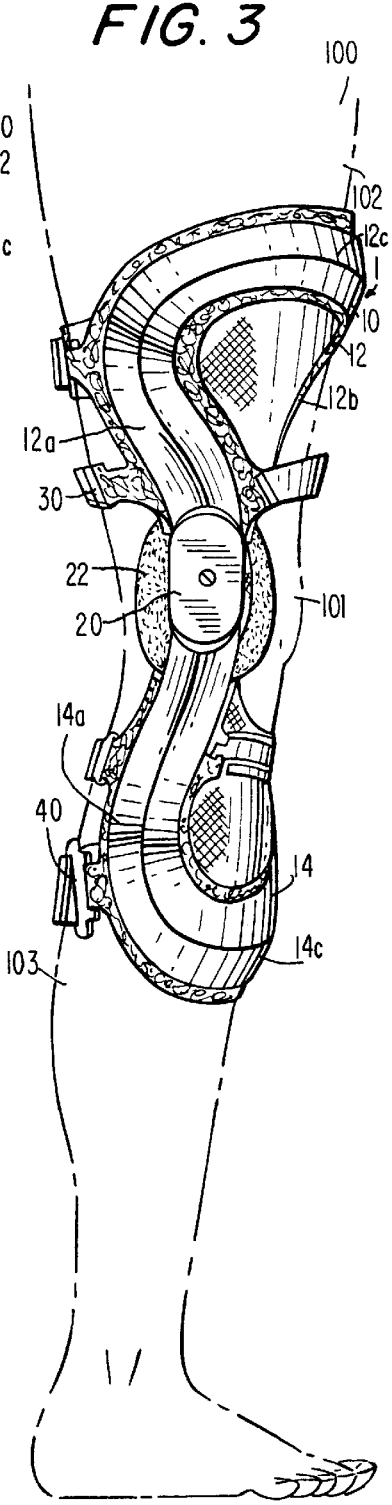

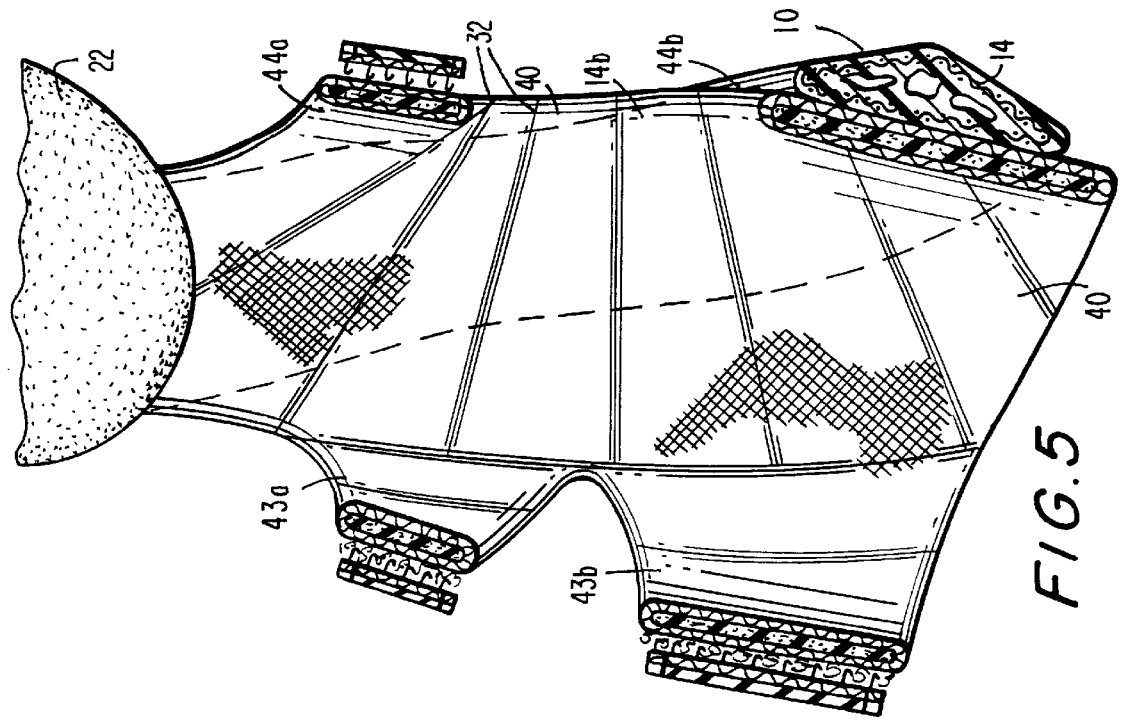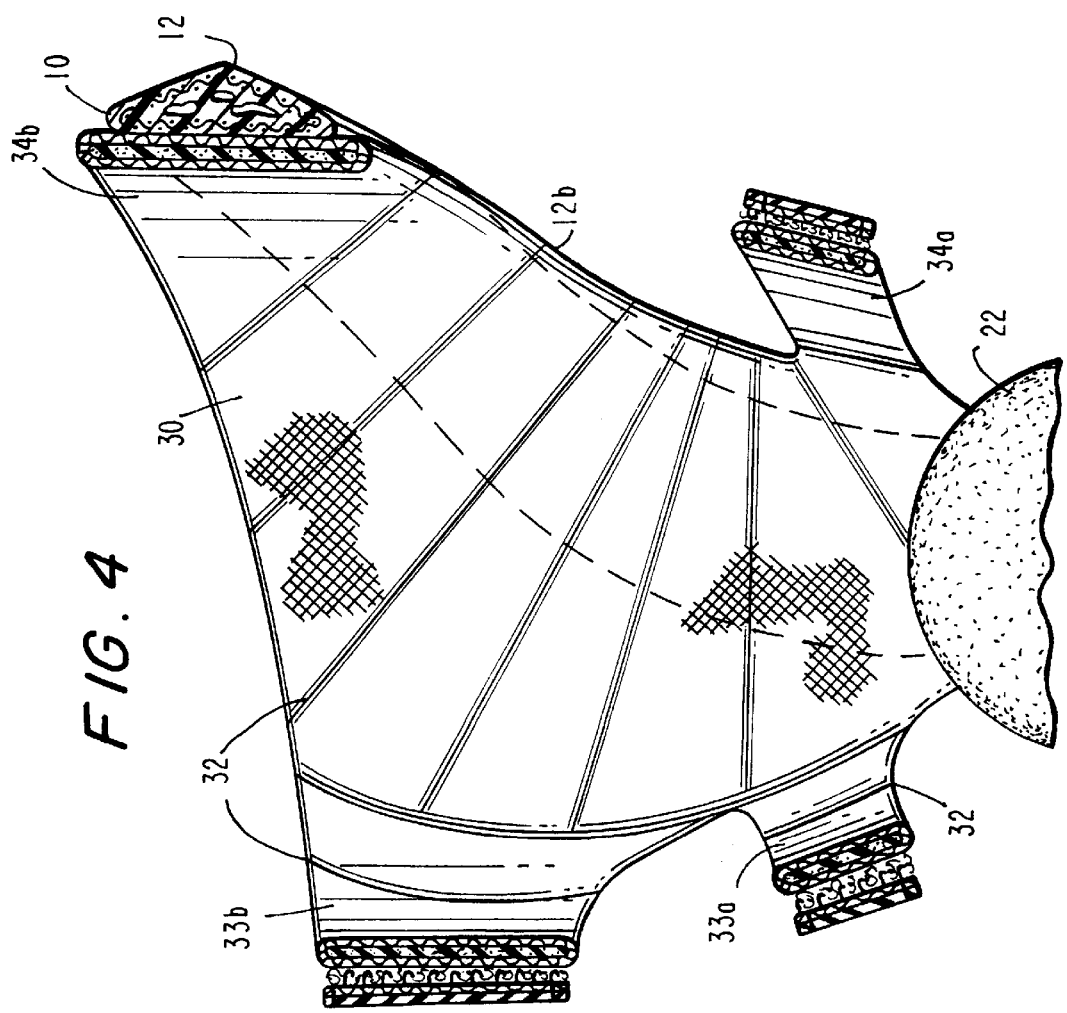

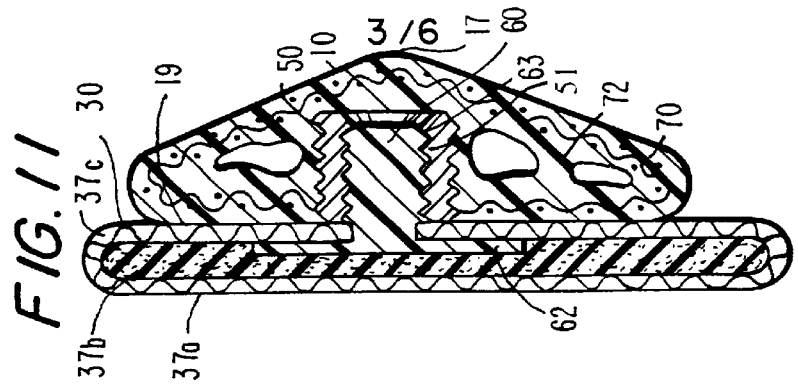
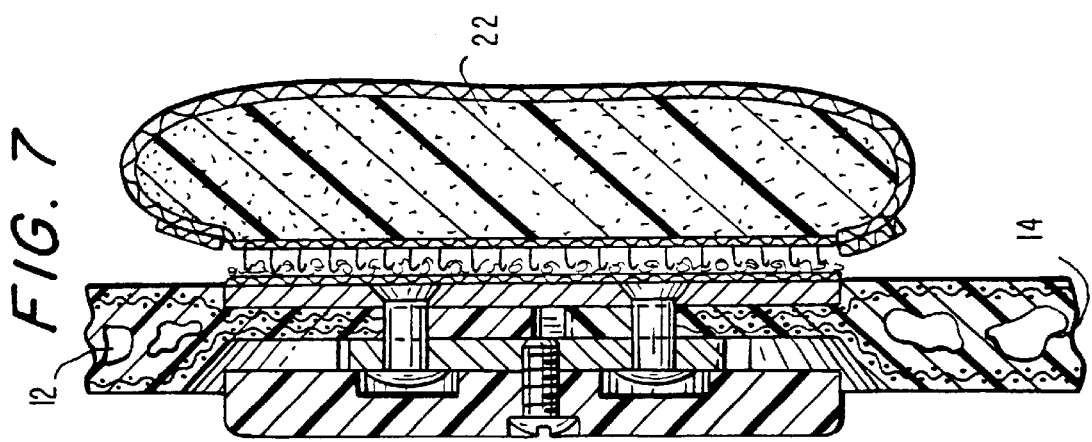
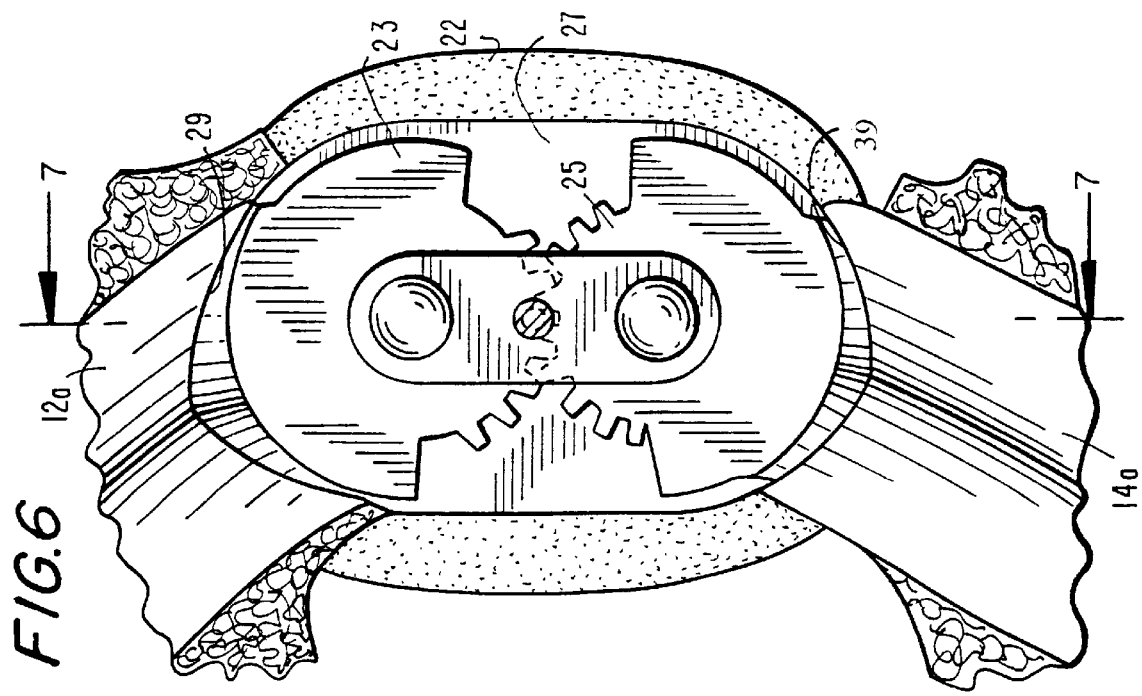

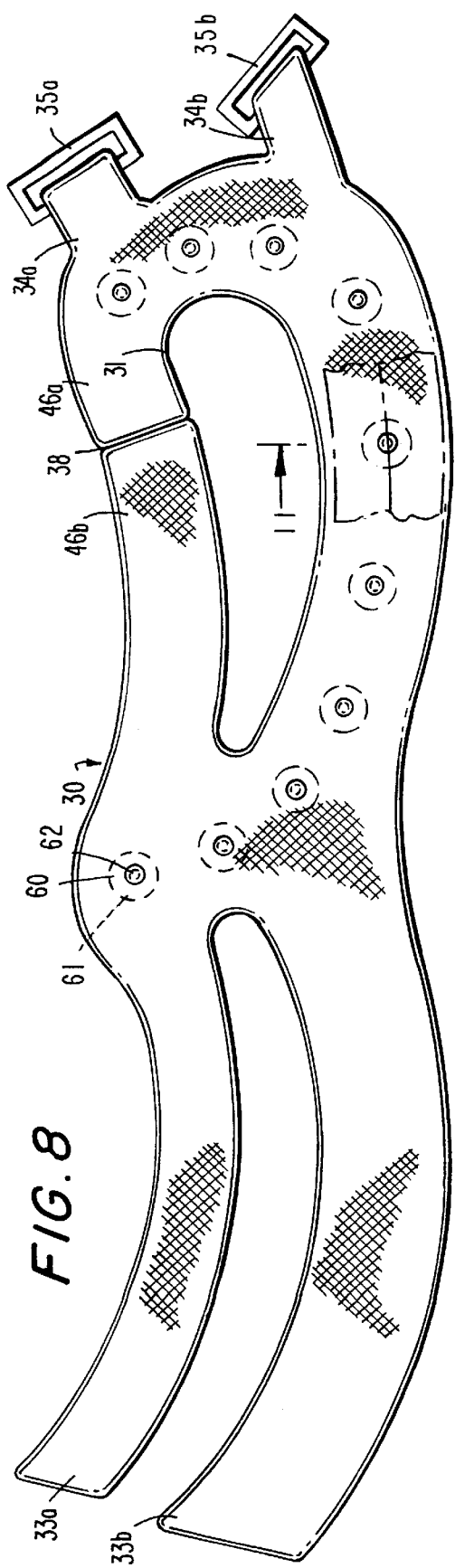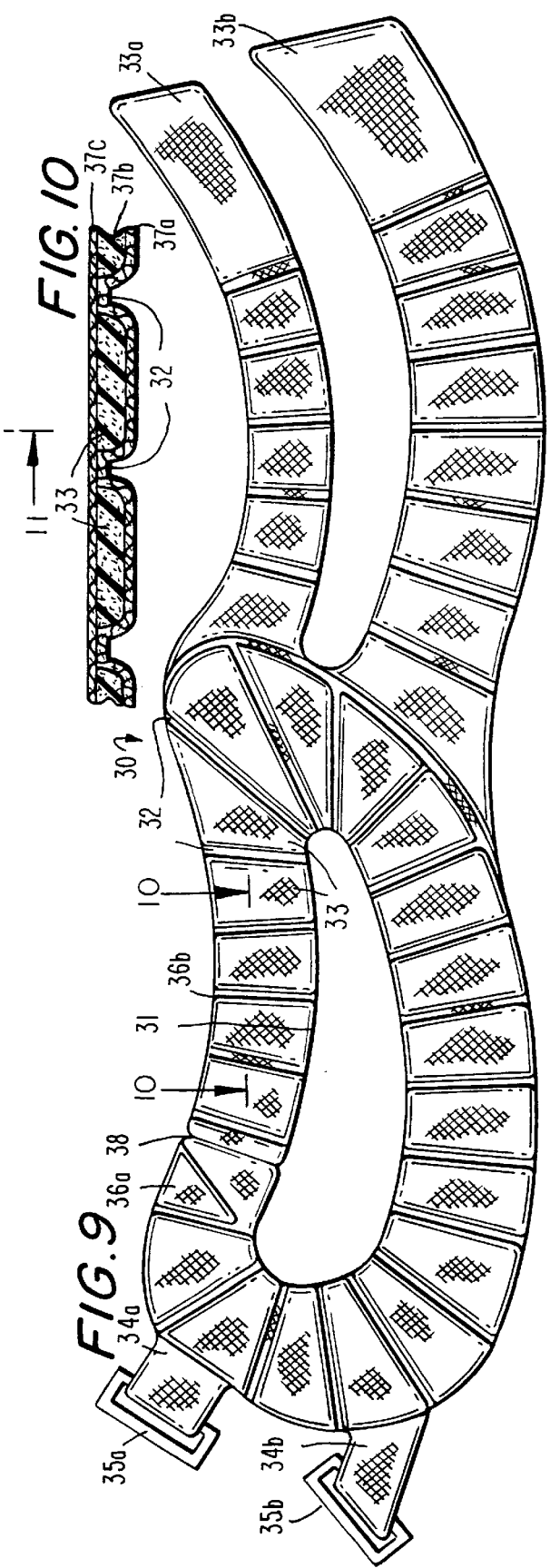

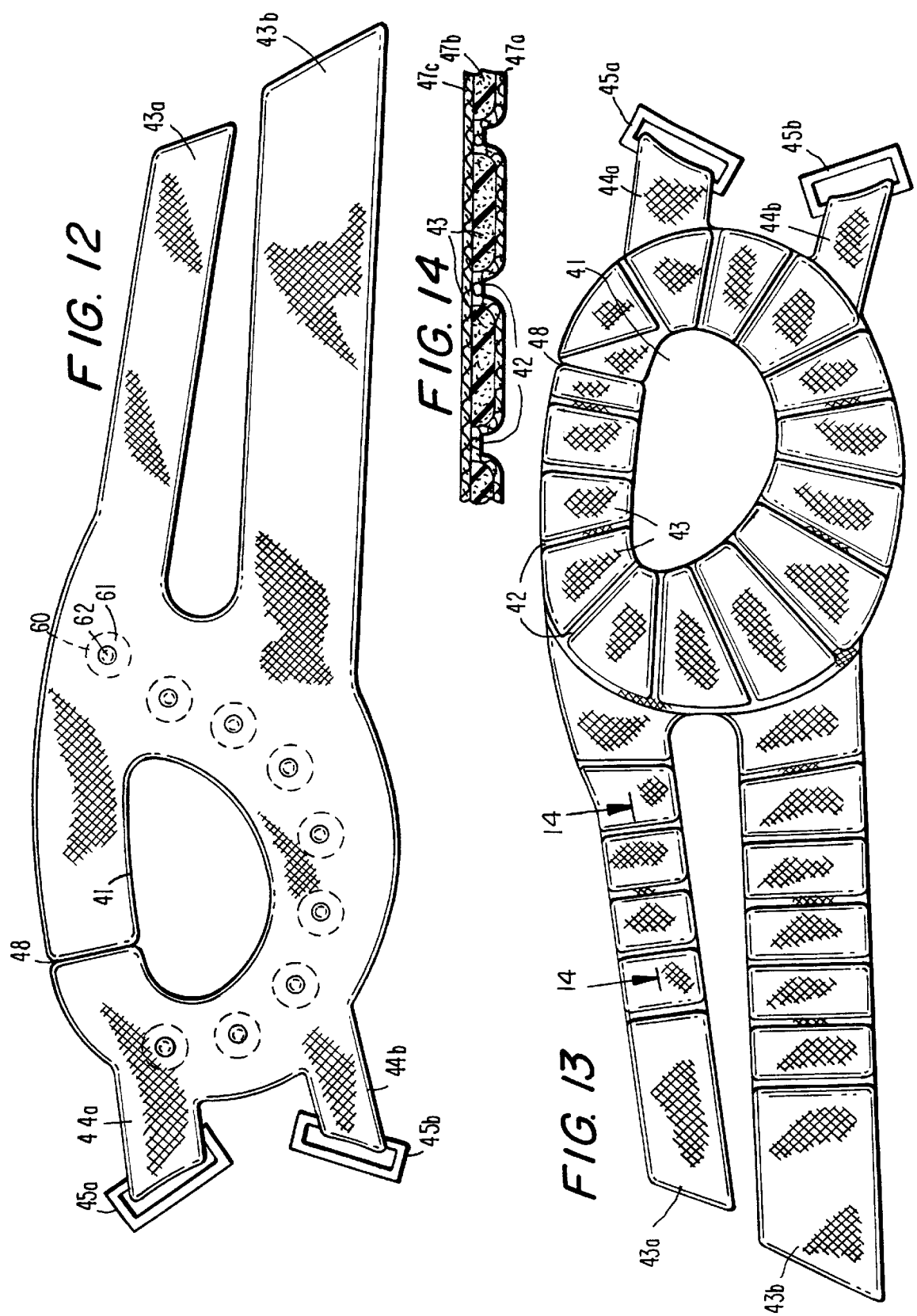

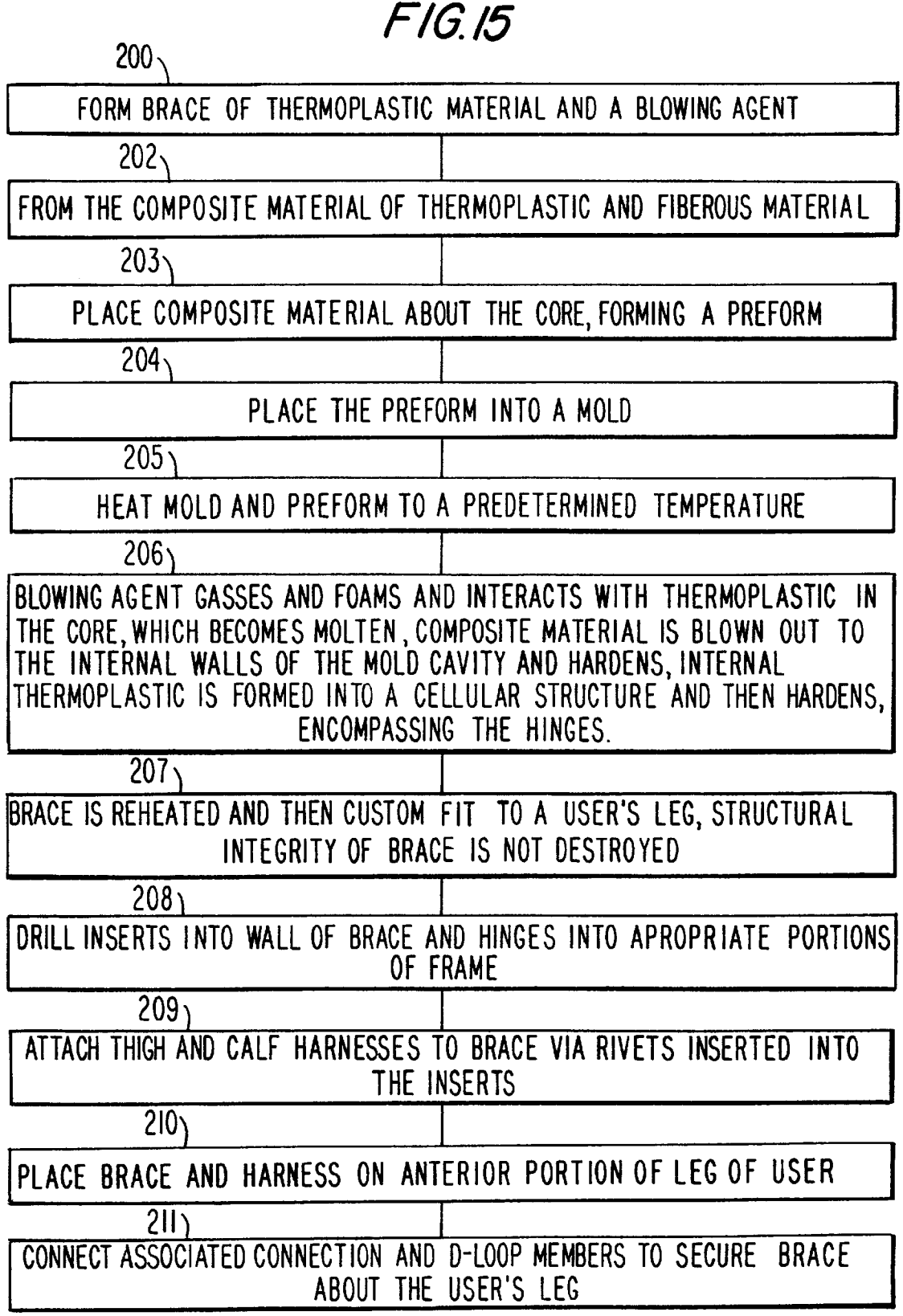

LEG BRACE

CROSS-REFERENCE TO RELATED APPLICATIONS

This application claims the benefit of U.S. provisional application Ser. No. 60/008,343, filed on Dec. 7, 1995, currently pending.

BACKGROUND OF THE INVENTION

This invention relates generally to a custom formed leg brace to stabilize an unstable knee during various activities and the process for manufacturing such a brace, and more particularly to a leg brace which is lighter, stronger and more comfortably controls rotation or other tibial movement than prior art braces.

After injury to the leg, and more particularly the knee, it is recommended practice to stabilize the knee and prevent rotation of the leg utilizing a brace as is known from U.S. Pat. No. 4,620,532.

Prior art leg braces essentially come in two forms. The first, completely custom braces, require the making of a plaster cast of a user's leg, the transport of this plaster cast to the factory, and thereafter the fabrication of a leg brace from scratch which is custom fabricated to fit the leg cast. This process is satisfactory, however the procedure is expensive and very time consuming. Alternatively, it is possible to purchase an "off the shelf" brace, which come in a variety of sizes, but are not custom made for the user's leg. This brace is also satisfactory, however, while the user is able to begin use of the leg brace immediately, the fit of the brace may not be precise, and as such the protection needed by the user of this brace may not be provided by this type of brace. Therefore, it would be desirable to provide a brace which was less expensive and had less lead time to produce, such as the "off the shelf" brace, but provided a tailored fit, such as the custom fabricated brace model.

In prior art leg braces, typically a very complicated and heavy strap assembly is used to retain the structural portion of the brace against the knee or leg. Typically, this strap assembly consists of any number of Velcro® straps riveted to the outside of the structural portion of the brace. Thereafter, these straps are interwound and wrapped about the user's legs in a specific fashion, thereby pushing the brace towards the user's legs from the outside of the brace. This resulted in braces which were very cumbersome and heavy, since each strap requires at least one metal rivet connected to the outside of the structural portion of the brace to retain the straps connected to the brace. Additionally such braces require many parts such as frame pads, hook and loop straps, strap pads, and an under sleeve. Also, the construction of such a brace is time consuming and expensive since each rivet and strap must be individually connected to the brace. Additionally, these external retention mechanisms are not visually pleasing.

Often, prior art leg braces are formed using a thermosetting material and process. This process to form a brace requires complex forming steps including the proper mixing of chemicals at precise temperatures. Furthermore, the by products of thermosetting are noxious fumes and chemical by products which are harmful to the environment or require great care in disposal.

Prior art leg and knee braces have been satisfactory. However, they also suffer from a number of defects.

Both of the prior art leg and knee braces are very heavy. In order to provide sufficient structural integrity to the brace so that it may prevent unwanted movement in the leg or knee, the material used is of a metal or thermoset material which is very heavy, and as a result fatigues the user and limits the movement of the user of the brace because of the weight. Heavier braces tend to migrate down a user's leg, thereby reducing the efficiency of the brace.

Next, the prior art leg and knee braces do not sufficiently protect against rotation of the tibia. Specifically, after a user has suffered an injury which causes any ligimental instability, such as an anterior cruciate ligament (ACL) tear (by way of example), the tibial bone not only has a tendency to move forward (anteriorly), but also rotates (in other situations, the tibia might move in other directions). However, the prior art leg brace which is designed to employ a transverse structural member across the front of the user's leg in order to restrict any anterior tibial movement does not address any of the rotation or other directional movement problems associated with ligament instability. Additionally, since this transverse structural member comes into contact with the tibia at only one point, any force imparted to the brace will be transferred to the point of the tibia in contact with the structural member, thereby causing undue pain for the user, and possibly precluding the user from sufficiently tightening the brace to provide the required support. It would be beneficial to provide a leg brace which is rigid but light, and addresses both the anterior movement and rotational movement of the tibia, while being comfortable for the user.

All braces must be retained tightly against the leg of the user to be effective. Straps on prior art braces do not provide any mechanism to enhance the grip of the strap by the user. It would be beneficial to provide a strap with a grip enhancing feature to assist the user in pulling the brace tightly to a users leg.

Finally, these multiple strap harness systems often require the user to over or underlay the straps in a particular manner so as to insure proper use of the brace. However, one who is not experienced in the use of such a brace may attach the straps improperly, therefore reducing the effectiveness of the brace. Additionally, to properly put on the brace takes a long time for a user. Since the straps are connected to the outside of the brace, and the brace is pushed towards the leg, it may be uncomfortable for the user, and additionally the brace may shift since only the hard structural portion of the brace is being retained against the leg by straps situated on the outside thereof. Adding to the discomfort is the requirement of an underbrace sleeve worn about the user's leg. Therefore, it is desired to provide a leg brace which overcomes the problems of the prior art and does not utilize such a complicated strap system, but rather utilizes a simplified system for retaining the brace against the leg. Additionally, it would be desirable to provide a leg brace where the harness system rather than being riveted to the outside of the brace, was riveted to the inside of the brace so that the brace could be pulled toward the leg, and be more surely retained on the user's leg and the harness would be in contact with the leg rather than the structural portion of the brace, thereby improving the fit and comfort of the brace and precluding the requirement of any underbrace sleeve.

SUMMARY OF THE INVENTION

Generally speaking, in accordance with the invention, a leg brace is provided for preventing rotation or anterior movement of the tibia, and movement of any other portion of the knee or leg. The leg brace is formed with a frame formed of at least a thermoplastic material and including a thigh cuff and a calf cuff. The leg brace also includes first and second hinge members connecting the thigh cuff and the calf cuff, and for allowing the thigh cuff to pivot relative to the calf cuff. The leg brace also employs a thigh harness fixed to the thigh cuff of the frame, the thigh harness member being retained adjacent a user's leg during use and a calf harness fixed to the calf cuff of the frame, the calf harness being retained adjacent a user's leg during use. The leg brace may be further formed with a tibial restricting portion being formed by part of the lower portion of the frame. The tibial restricting portion being situated so as to run along and substantially parallel to the medial shaft of a user's tibia during use, thereby preventing any unwanted movement or rotation of the user's tibia. The leg brace can further be formed with a triangular cross-section to increase its strength. The harnesses can be formed with quilts formed therein to improve the comfort and the moisture wicking ability of the brace. Finally, the frame may be formed with rivet inserts formed on the inside surface there so that the harnesses can be connected to the inside surface of the frame.

The invention also comprises a method for forming such a brace, including the steps of forming a brace core of a mixture of a thermoplastic material and a blowing agent in the general shape of a brace to fit user's leg and then placing a composite material formed of at least a thermoplastic material and a fibrous material in contact with the core. Next, the core and composite material are placed in a mold and the mold is heated to a temperature sufficient to allow the thermoplastic material to become molten, causing the blowing agent to expand and force the composite material against an interior wall of the mold cavity, and for the blowing agent to form the thermoplastic material in the core into an internal cellular structure. Thereafter, the mold and its constants are cooled. Next, the leg brace is reheated to a temperature sufficient to allow the thermoplastic material to become malleable, but not sufficient to allow the thermoplastic material to become molten and destroy the structural integrity of the leg brace, and is reshaped about the leg of the user or a model representation thereof to provide a custom fit. This method can also be used to form and reform any structural member, and is not limited to the formation of a leg brace.

Finally, the harness system for the leg brace is formed of a circular portion for attaching to the internal surface of a leg brace, at least one receiving arm having a first and a second end, the first end fixed to the circular portion and at least one attaching member associated with and fixed to the second end of the at least one receiving arm. Also included is at least one first connection arm associated with the at least one attaching member and the at least one receiving arm, and having a first and second end, the first end being fixed to the circular portion. The second end of the at least one connection arm being fixed to the associated at least one attaching member during use, whereby the harness and the leg brace are retained in a fixed position against a user's leg. Preferably, each arm includes a gripping member to assist a user in tightening the associated arm, and improve the aesthetics of the brace.

Accordingly, it is an object of this invention to provide an improved leg brace.

Another object of the invention is to provide an improved leg brace wherein several portions of the brace conform to the medial shaft of the tibia, thereby preventing rotation or other undesirable movement of the tibia.

A further object of the invention is to provide a leg brace formed of a strong, super light material to prevent user fatigue and to maintain the brace in its proper position.

Still a further object of the invention is to provide a leg brace which may be first heat formed into general sizes, and thereafter may be reheated in order to be custom fit to a user's leg without destroying the structural integrity of the brace so that a custom brace may be provided.

Still another object of the invention is to provide a brace which has a simplified harness construction.

Yet another object of the present invention is to form a leg brace with a harness system situated inside the brace rather than outside the brace, whereby the brace is pulled towards the leg and remains in position more easily.

Yet a further object of the invention is to provide a harness system for use with a leg brace which is more lightweight, easier to use, has less parts, is easier to assemble and is cooler than conventional leg brace strap assemblies.

Still another object of the present invention is to provide a leg brace whereby the internal harness system is connected to the brace from the inside surface thereof, the connecting members being retained within the internal structure of the leg brace.

Yet, another object of the invention is to provide a brace using environmentally friendly materials and processes.

Still a further object of the invention is to provide a method for forming and then reforming a structural member.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which are adapted to affect such steps, all as exemplified in the following detailed disclosure, and the scope of the invention will be indicated in the claims.

BRIEF DESCRIPTION OF THE DRAWINGS

For a fuller understanding of the invention, references is had to the following description taken in connection with the accompanying drawings, in which:

FIG. 1 is a front elevational view of a leg brace worn by a user and constructed in accordance with the invention;

FIG. 2 is a rear elevational view of the leg brace of FIG. 1;

FIG. 3 is a side elevational view of the leg brace of FIG. 1;

FIG. 4 is a cross-sectional view taken along line 4—4 of FIG. 1;

FIG. 5 is a cross-sectional view taken along line 5—5 of FIG. 1;

FIG. 6 is a side elevational view of a hinge mechanism used in the leg brace of FIG. 1;

FIG. 7 is a cross-sectional view taken along line 7—7 of FIG. 6;

FIG. 8 is a bottom plan view of the thigh harness of the leg brace of FIG. 1;

FIG. 9 is a top plan view of the thigh harness of the leg brace of FIG. 1;

FIG. 10 is a cross-sectional view taken along line 10—10 of FIG. 9;

FIG. 11 is a cross-sectional view taken along line 11—11 of FIG. 8;

FIG. 12 is a bottom plan view of the calf harness of the leg brace of FIG. 1;

FIG. 13 is a top plan view of the calf harness of the leg brace of FIG. 1;

FIG. 14 is a cross-sectional view taken along line 14—14 of FIG. 13; and

FIG. 15 is a flowchart representing the steps for producing the leg brace in accordance with the invention.

DETAILED DESCRIPTION OF THE PREFERRED EMBODIMENTS

Reference is first made to FIGS. 1, 2 and 3 which generally depict a leg brace 1 which is designed to retain the relative positioning of a user's upper and lower leg, knee and tibia. Leg brace 1 includes a frame member 10 divided into thigh cuff 12 and a calf cuff 14, and a calf harness 40, and thigh harness 30.

Thigh cuff 12 includes a lateral portion 12a extending along the lateral side of a user's leg, and a medial portion 12b extending along the medial side of a user's leg 100 to provide structural support thereto. A transverse portion 12c extends across a user's thigh 102 from lateral portion 12a to medial portion 12b to form a unitary thigh cuff 12. Transverse portion 12c is curved to match the curvature about a user's thigh. This transverse portion 12c crosses over user's thigh 102 to provide structural support to leg brace 1 while retaining the relative positioning of leg brace 1 against user's leg 100. Lateral portion 12a, medial portion 12b and transverse portion 12c in conjunction provide structural support for user's leg 100 by rigidly fixing the relative positioning of user's thigh 102 and user's knee 101. Hinge members 20, 21 are affixed to thigh cuff 12 at lateral portion 12a and medial portion 12b, respectively.

As is shown in FIG. 11, threaded inserts 50 are inserted into the surface 19 of thigh cuff 12 which faces the user's thigh 102. Inserts 50 are threaded on their inner circumference and their outer circumference. Thigh cuff 12 is retained in contact with user's thigh 102 by thigh harness member 30 (FIG. 4), as will be discussed below.

FIGS. 8–10 show a bottom plan view, top plan view and a cross-sectional view, respectively, of a right thigh harness 30. A left thigh harness 30 would be the mirror image of that shown in FIGS. 8–10. As shown in FIG. 8, thigh harness 30 is formed with an elliptical portion 31, first and second connection arms 33a and 33b, respectively, first and second receiving arms 34a and 34b, respectively, and first and second D-Loop members 35a and 35b, respectively. Elliptical portion 31 is further formed with a cut 38 therein. This cut forms anterior arms 36a and 36b in elliptical portion 31.

This harness may be formed of any resilient material which may be retained sufficiently against the user's leg so as to retain the position of the brace. However, in a preferred embodiment, the brace is formed of a three layer material, as is shown in FIG. 10 and in FIG. 11. In a preferred embodiment, harness 30 may be formed of a cushion layer 37a, a closed cell material layer 37b, and a tear resistant material layer 37c as shown in FIG. 10. As is shown, these three layers are bonded together, so as to form a singular structure laminate. As is additionally shown in FIG. 10 as well as FIG. 9, the cushion layer 37a is formed with quilts 32 formed therein separated by embossed sections 33. These quilts allow for easy bending of the harness to better facilitate shape change of the harness so it can be better fit to the brace and can prevent bunching when the brace is fixed to a user's leg. Embossed sections 33 assist in the wicking of moisture away from the user's body. Layer 37b is formed of a closed cell material so as to not retain water from the user or from any external source. In a preferred embodiment, this close cell material is an EVA fiber and more preferably may be formed as a layer 3/16" thick. The cushion and tear resistant material may be formed of any material which is sufficient to act as a cushion, while allowing for quilts to be formed therein in the case of cushion 37a, and any tear resistant material which is malleable enough to be maintained and to make contact with the close cell structure 37b during use of the harness system. Further layers may be added to the material to enhance the performance of the harness.

As is additionally shown in FIG. 8, thigh harness 30 is also formed with rivets 60 contained therein. Each of these rivets is formed with a stem 62 and a perpendicular planar portion, or head 61 forming a rivet connected thereto. Head 61 of each rivet 60 is retained between layers 37b and 37c of FIGS. 10 and 11, stem 62 extending through layer 37c. Stem 62 is further formed with retaining blades 63 formed thereon. During use, when rivet 60, and stem 62 thereof, is inserted into retaining insert 50, contained in frame 10, retaining blades 63 retain rivet 60 within retaining insert 50 by engaging with retaining insert threads 51, as is shown in FIG. 11. These rivets 60 may also be inserted into blind holes drilled in frame 10.

Calf cuff 14 of frame 10 of leg brace 1 includes a lateral portion 14a, situated on the lateral side of user's calf 103, a medial portion 14b, situated on the medial side of user's calf 103, these lateral and medial portions 14a and 14b providing support for the associated sides of user's leg 100. Calf cuff 14 is further formed with a transverse portion 14c which extends from medial portion 14b to the area of user's leg 100 where the tibia (not shown) is located. This transverse portion 14c is curved to conform to the shape of a user's leg. Similar to thigh cuff 12 of frame 10 of leg brace 1, calf cuff 14 of frame 10 of leg brace 1 is fixed to first and second hinge members 20 and 21 at lateral portion 14a and medial portion 14b. Therefore, when first and second hinge members 20 and 21 are situated against user's knee 101, calf cuff 14 of frame 10 is positioned adjacent user's calf 103 to contact the tibia.

Calf cuff 14 is further formed with a tibial restricting portion 15 extending substantially in the medial direction down and away from medial portion 14b curved in a direction towards lateral portion 14a and transverse portion 14c and running essentially parallel to the medial shaft of the tibia of user's leg 100 and thus remaining in contact therewith. Tibial restricting portion 15 is situated in such a parallel manner so as to retain the tibia from moving in the anterior, posterior, medial, or lateral directions, restrict any rotation of the tibia, and further to disperse any force imparted on the brace over a wider area of the tibia. As with thigh cuff 12, inserts 50 are disposed within a surface 19 of calf cuff 14 facing the user's leg (FIG. 11).

As noted above, prior art braces do not contain this tibial restricting portion, but rather transverse portion 14c would extend completely across the front of the user's leg 100. Since the portion of the structural member (transverse portion 14c) in the prior art brace would be substantially perpendicular to the direction of the tibia, while this transverse member might be sufficient to resist any anterior motion of the tibia, there would be no restriction of any rotation of the tibia since no portion of the structural member would be on either side of the tibia, next to the tibia, in order to restrict this rotation. In addition, this transverse member would cross the tibia at only one point. Therefore, any force imparted on the brace would be transmitted directly to that point of the tibia, thereby causing discomfort to the user.

Therefore, leg brace 1 constructed in accordance with the invention, further employing tibial restricting portion 15, allows for the restriction of any unwanted movement of the tibia, decreases the discomfort of the user when wearing the brace, and provides sufficient rigid and structural support between user's thigh 102, user's knee 101 and user's calf 103 to resist any further unwanted movement of the user's thigh 102 or user's calf 103 relative to user's knee 101. Calf cuff 14 of structural member 10 of leg brace 1 is retained against user's leg 100 through the use of a lower harness 40 which will be described below.

A calf harness 40 is affixed to calf cuff 14 (FIG. 5) to maintain a user's calf and tibia secure within the brace. Like harness 30, harness 40 is formed with an elliptical portion 41 as shown in FIGS. 12–14, first and second connection arms 43a and 43b, first and second receiving arms 44a and 44b and first and second attaching members 45a and 45b. Again, in a preferred embodiment, harness 40 may be formed of a cushion where 47a, a closed cell material 47b and a tear resistant material layer 47c, as shown in FIG. 14. The cushion layer 47a may be formed with quilts 42 formed therein separated by embossed sections 43. Rivets 60 having stem 62, head 61 and blades 63 are disposed between layers 47b and 47c of harness 40 and oriented so that the blade 63 and stem 62 may be received by a corresponding retaining insert 50 within calf cuff 14.

Thigh and calf cuffs 12 and 14 of frame 10 are formed of a structurally rigid, lightweight material. As is shown in cross section in FIG. 11, frame 10 is formed with a rigid external layer 70, and a cellular core 72. As is also shown in FIG. 11, preferably frame 10 has a substantially triangular cross section, the apex 17 of which is directed away from the user's leg, while the surface 19 which faces the user's leg, and in to which the harness system (discussed below) is anchored forms the triangle's base. In a preferred embodiment, the rigid external layer may be formed of a thermoplastic composite material in which a fibrous material is combined with a thermoplastic resin. Preferably, this thermoplastic resin is polypropelene, but may comprise any type of thermoplastic resin. In addition, the fibrous material is preferably fiberglass, but may also comprise carbon, KEVLAR fibrous material, or any other fibrous material. The internal core has a cellular structure, the structural elements of the cell also being formed of a thermoplastic material, preferably the same thermoplastic material used in the composite material. Frame 10, formed of this dual layer material, is provided with structural integrity by the rigid external structure and the structural integrity is increased by this internal cellular structure provided of thermoplastic material and triangular shape. Additionally, the cellular internal structure allows the brace to be lighter than prior art braces while retaining the structural rigidity. Finally, the triangular cross sectional shape of frame 10 also helps provide structural integrity for the brace.

These thigh and calf cuffs 12 and 14, respectively, are connected to each other via first hinge member 20 and second hinge member 21 as is known in the art from U.S. Pat. No. 4,620,532 or by the gearing mechanism of FIG. 6, by way of example.

These first and second hinge members 20 and 21 may include gears 23, 25 which engage to allow for the relative movement of either the thigh cuff 12, calf cuff 14, or movement of both thigh cuff 12 and calf cuff 14 with respect to the first and second hinge members 20 and 21, while first and second hinge members 20 and 21 are retained in their original position relative to the user's knee. A cover plate 27 protects gears 23, 25. Portions 12a, 14a are formed with recesses 29, 39 to provide clearance about cover plate 27. First and second hinge members 20 and 21 further comprise respective condyle pads 22 fixed on the internal surface thereof in order to cushion a user's knee against first and second hinge members 20 and 21. In a preferred embodiment, these condyle pads may be fixed to the hinge members using a hook and latch type fastener. However, these condyle pads may be affixed to hinge members 20 and 21 in any other fashion, to be either removable or permanently fixed (FIGS. 6 and 7).

Leg brace 1 is preferably designed so that first and second hinge members 20 and 21 are retained at the level of a user's knee axis, thereby allowing the thigh cuff and calf cuff 12 and 14 of frame member 10 of leg brace 1 to be pivoted about the knee in coordination with any movement of a user's knee 101. In this manner, brace 1 follows the movement of the leg as it moves so as not to restrict bending of the leg about the knee. With first and second hinge members 20 and 21 positioned at the user's knee, thigh cuff 12 of frame member 10 of leg brace 1 would therefore be positioned adjacent the user's thigh 102 and releaseably fixed thereto by harness 30.

The steps for formation of upper and lower portions 12 and 14 of structural member 10 of leg brace 1 will now be described with reference to the flowchart of FIG. 15. As is shown in FIG. 15, the frame 10 is formed in step 200, a brace core comprised of a mixture of a thermoplastic material and a blowing agent is formed into the general shape of a brace conforming to a leg of a particular size. Next, in step 202, a composite material is formed of a thermoplastic resin and another type of fibrous material, as described above. Next, in step 203, this composite material is placed around the core of thermoplastic material and blowing agent, forming a sleeve, and is thereafter formed into what is called a "preform". In step 204, a first preform which will eventually be formed into thigh cuff 12 of frame 10, and a second, calf cuff preform which will be formed into calf cuff 14 of frame 10 are both placed in the mold. In step 205, the mold housing, the preform for the thigh cuff and calf cuff, are heated. In the preferred embodiment, the mold has a substantially triangular-shape formed therein to provide a substantially triangular cross section to the molded parts.

In step 206, the mold and components contained therein are heated to a temperature sufficient that the blowing agent contained in the core of the brace begins to gas and foam. This temperature is also sufficient so that the thermoplastic material becomes molten and begins to flow. The gassing or foaming of the blowing agent then builds up pressure within the composite material, and the composite material is blown out through the internal pressure into contact with the internal walls of the mold cavity. Additionally, since the blowing agent is foaming and gassing, the molten thermoplastic material is formed into a cellular structure inside the composite sleeve, as well as formed into a solid structure intertwined with the composite material against the internal wall of the mold cavity. As the temperature of the components are thereafter lowered, the composite material, and the thermoplastic material hardens in its current arrangement, producing a structurally sound and rigid external layer 70 (originally the composite sleeve) and a cellular thermoplastic internal core 72 (FIG. 11). The brace is now formed to a general shape and size, but is not yet custom formed to an individual user's leg. The triangular cross section provides rigidity to the brace even though the inner layer of frame 10 is formed of a foam, so that strength is not sacrificed for reduced weight, although the shape need not be triangular, it is preferred in this embodiment. Furthermore, in a preferred embodiment, the sections of portions 12a, 12b, 14a, 14c which will eventually be adjacent hinges 20, 21 are molded with a curved clearance to allow pivoting of cuffs 12, 14 about any hinge covering plate.

Next, in step 207, when it is necessary to customize the brace to a user's leg, the brace is reheated to a temperature lower than that originally used to form the brace. Thus, the brace is reheated to a temperature at which the thermoplastic material softens for reforming of the cuff's shape, but which does not allow the thermoplastic to change to a complete molten state, and which does not affect the structural integrity of the brace. Thus, when the brace is reheated, the brace is then shaped to a specific user's leg or model representation thereof, so that a custom fit is provided. Next, in step 208, retaining inserts 50 can be drilled into the base of the triangular portion of rigid external structure layer 70 and hinges 20 and 21 can be drilled into portions 12a, 12b, 14a, 14b of thigh and calf cuffs 12 and 14. These inserts can be used in step 209, to attach the thigh and calf harnesses 30 and 40, as will be described below. However, as is shown in FIG. 11, it is clear that a rivet member 60 which is fixed to either upper or lower harness member 30 or 40 (30 in FIG. 11) is inserted into retaining insert 50 so as to retain the upper or lower harness member 30 or 40 against the rigid external structure layer 70 of structural member 10.

In alternative embodiments, the retaining insert 50 may be inserted into the brace during an earlier step. Specifically, first, the retaining inserts may be placed into the mold with the preform and hinges during step 204 and thereafter when the mold is heated (step 205) and the blowing agent forces the thermoplastic and the composite material against the mold (step 206), the rivets may be engulfed and thereby incorporated into the structure of the brace. Alternatively, between steps 206 and 207, it is possible to drill the retaining inserts 50 into the structure of the brace after the brace is formed and cooled, but before the brace is reheated for custom fitting.

Additionally, the outside of the brace may be painted for various colors. Alternatively, colors may be imparted on the brace in two ways. First, a pigment may be added to the composite fiber material, such as the fiberglass, before it is formed into a composite material. Thereafter, this material will be colored when formed into the brace. Alternatively, a gel coat pigment may be placed into the internal surface of the mold before the preform is placed into the mold. Thereafter, when the mold is heated (step 205) and the preform is formed into the brace by the flowing thermoplastic material (step 206), the gel coat will be incorporated into the brace, and therefore the color will be imparted to the brace during the forming process. Further, a pigment may be added to a thermoplastic film, which is the same resin as that used in the composite material. This film may be wrapped around the preform before molding. When the preform is then heated, the film will melt onto the surface of the cuff, providing the desired color.

Finally, although the method set forth above shows the hinges being drilled into the frame, it is possible to form thigh and calf cuffs 12 and 14 of frame 10 in step 204 with hinges 20 and 21 being placed in the mold with the preforms. Upon heating the flowing material encompasses enough of hinges 20, 21 to bond them to portions 12a, 12b, 14a, 14b to form a substantially unitary unit without inhibiting movement of the hinge.

Next, as is shown in step 209, the rivet members of the harness portion may be inserted into retaining inserts 50 and thereby the harness and rivet would be attached to calf cuff 14 of frame 10. Rivet heads 61 are formed in a size large enough to distribute force imparted thereon from any pulling force of the brace. Additionally, rivet head 61 are formed large enough to retain a relatively large portion of calf harness member 40 against calf cuff 14 of structural member 10.

During the use of lower harness member 40, first and second D-Loop members 35a and 35b are respectively permanently fixed to first and second receiving arms 34a and 34b. These D-Loop members may be attached to the receiving arms in any conventional manner, and may be of any conventional type. However, in a preferred embodiment, each of these D-Loop members are formed as a rectangular member, and each of the receiving arms are looped through the associated D-Loop member around one side of the associated attaching D-Loop member, which each are attached back upon themselves, thereby capturing the associated D-Loop member within the associated attached loop of the associated attached receiving arm. When upper harness member 30 is used in connection with the brace, elliptical portion 31 is retained on the anterior portion of the user's leg, whereas first and second connection arms are wrapped behind the user's leg, to the posterior area, and are thereafter connected to first and second attaching members, respectively. This connection may be made by any conventional connecting means, however in a preferred embodiment, a hook and loop type fastener is used which both parts of the fastener are fixed to first and second connection arms 33a and 33b. The harness material may also function as the loop portion of the fastener, thereby precluding the need to further fix a loop portion. Specifically, this hook and loop fastener is permanently fixed to the harness to allow the user to properly attach and detach the brace. During attachment, the connection arm is fed through the opening of the respective attaching member, and thereafter folded back upon itself to retain the brace on a user's leg. Upon this folding, the hook and loop fasteners are engaged, and the harness system is retained in position. Harness 40 is arranged in a similar manner.

As shown in FIGS. 1–3, the brace and harness are placed on the anterior portion of the leg of the user in a step 210, and in step 211 the associated connecting arms and attaching members are connected to secure the brace about the user's leg. As is shown in FIG. 3, frame 10 is retained against the leg of the user by the harness members 30 and 40 being attached securely in direct contact with the leg. As can be shown in FIG. 1 cuts 38 and 48 in elliptical portions 31 and 41 respectively rest on the anterior portion of the user's leg. Anterior arms 36a and 36b, and 46a and 46b are then releasably fixed to each other with a fastener to assist in fixing the size of the brace, and retaining the brace on the leg of the user. Additionally the anterior distal strap further assists in tibial control, and the anterior proximal strap as well as all other straps further assists in preventing pistoning or movement away from the knee. Furthermore, as is shown in FIGS. 1–3, the various connecting arms, receiving arms and attaching members are used to retain the harness, and therefore the brace attached thereto in the proper position against the posterior portion of the user's leg. Because the harness members are attached to the frame 10 of the brace from the inside thereof, the harness members pull the brace towards the leg with the harness situated between the leg and the brace. Therefore, the brace is more comfortable to wear since the harness system is not impeded by the brace in coming into contact with the user's leg. Also, an underbrace sleeve is not required since the harness system provides sufficient comfort for the user. The brace is more comfortable to wear, and is retained in its optimal position more easily, and for a longer period of time.

Additionally, since the rivets are retained in the internal portion of the brace, rather than the external, the brace is much more appealing to the eye and is far less bulky. Further, because the rivets are contained within the brace and do not require additional hardware to connect any straps to the brace or the rivets to the brace, the brace is further lightened over those braces of the prior art.

Forming frame 10 of a thermoplastic material is beneficial in that unlike thermoset material which is used in the prior art which is set once and then cannot be re-reformed, the thermoplastic material can be formed into a brace as described above, and then can be heated to a lower temperature at which the brace becomes malleable to allow the brace to be conformed for a custom fit to a user's leg, while not destroying the structural integrity of the brace. Additionally, while thermoset material shatters when it breaks from undue stress or a breaking force, the thermoplastic material employed in the invention does not break so catastrophically, but rather bends. Therefore, the thermoplastic material is far safer to use than the thermoset material. Additionally, the thermoplastic material is a better shock absorber than the thermoset material, therefore increasing the comfort of the brace to the user. Finally, during formation of the brace of the thermoplastic material, the gasses produced are environmentally safe and are not noxious, whereas the gasses produced during the thermoset material process are noxious, and are therefore not environmentally friendly. As a result, the manufacturing process is far more difficult, time consuming and expensive when the thermoset material is employed since these gasses must be properly dealt with and disposed of.

By providing a leg brace as constructed above, the leg brace of the invention overcomes the deficiencies in the prior art in that the leg brace is formed of a lightweight, strong material which can be heated and reformed to be custom fit, the upper and lower harnesses are each formed of single pieces of material, thereby simplifying the attachment procedure, each of the harnesses are connected to the inside of the leg brace so that the brace is pulled towards the leg and will remain on the leg for a longer period of time, and does not require that an underbrace sleeve be worn about the user's leg. Additionally, the brace of the invention is more comfortable for the wearer to use since structural portions of the brace are not retained directly against the user's leg, the brace contains a tibia retaining piece for specifically addressing tibial movement without imparting undue pressure on the tibia, and the rivets holding the harness are maintained internal to the brace so that these rivets do not show and may be smaller, and thus do not add substantial extra weight to the brace.

It is also noted that while the formation of a leg brace using this process has been described, this is for example only. The process including the reforming step can be used for the production of any other product including, but not limited to other body part braces, back braces, sporting equipment, tennis rackets, or any other products or structural members.

It will thus be seen that the objects set forth above, among those made apparent from the preceding description are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A leg brace, comprising:
    a frame formed of at least a thermoplastic material having a non-uniform density in cross-section, said frame including a thigh cuff and a calf cuff;
    first and second hinge members connecting said thigh cuff and calf cuff, and for allowing said thigh cuff to pivot relative to said calf cuff;
    a thigh harness fixed to said thigh cuff of said frame, said thigh harness being retained adjacent a user's leg during use; and
    a calf harness fixed to said lower portion of said frame, said calf harness being retained adjacent a user's leg during use.

2. The leg brace of claim 1, wherein each structural member of said frame is formed with a substantially triangular cross-section.

3. The leg brace of claim 2, wherein said substantially triangular cross-sectioned frame is formed with a rigid outer layer of thermoplastic composite material, and a less dense thermoplastic foam contained within said rigid outer layer.

4. The leg brace of claim 1, wherein at least one of said thigh harness and said calf harness are formed with quilts formed therein.

5. The leg brace of claim 1, wherein at least one of said thigh harness and said calf harness are attached to a surface of said frame facing the user's leg during use.

6. The leg brace of claim 5, wherein said frame is formed with rivet inserts formed on the inside surface thereof, said thigh harness and calf harness further containing rivets to be inserted into said rivet inserts to retain said harnesses against the inside surface of said frame.

7. The leg brace of claim 1, wherein said calf cuff includes at least a portion of said frame forming a tibial restricting portion, said tibial restricting portion being situated so as to run along and substantially parallel to the medial shaft of a user's tibia and to be maintained in contact with a user's tibia when a user's leg is placed within the brace, thereby preventing any unwanted movement or rotation of the user's tibia.

8. A leg brace, comprising:
    a frame having a thigh cuff and a calf cuff;
    a tibial restricting portion formed from at least a portion of said frame, said tibial restricting portion being situated so as to run along and substantially parallel to the medial shaft of a user's tibia and to be maintained in contact with a user's tibia when a user's leg is placed within the brace, thereby preventing any unwanted movement or rotation of the user's tibia; and
    first and second hinge members connecting said thigh cuff and calf cuff of said frame, and for allowing said calf cuff to pivot about the hinge relative to the thigh cuff.

9. The leg brace of claim 8, wherein said frame is formed of at least a thermoplastic material having a non-uniform density in cross-section.

10. The leg brace of claim 9, wherein each structural portion of said frame is formed with a substantially triangular cross-section.

11. The leg brace of claim 10, wherein said substantially triangular cross-sectioned frame is formed with a rigid outer layer of thermoplastic composite material, and a less dense thermoplastic foam contained within said rigid outer layer.

12. The leg brace of claim 8, filter comprising a thigh harness affixed to said thigh cuff and a calf harness affixed to said calf cuff.

13. The leg brace of claim 12, wherein at least one of said calf harness and thigh harness is quilted, said harness including at least one grip member thereon.

14. The leg brace of claim 13, wherein said frame is formed with rivet inserts formed on the inside surface thereof, said thigh and calf harnesses further containing rivets to be inserted into said rivet inserts to retain said harnesses against the inside surface of said frame.

15. The leg brace of claim 12, wherein said thigh harness and said calf harness are attached to an inside surface of said frame.

16. A leg brace, comprising:

a frame formed of at least a thermoplastic material;

a harness member fixed to an inside surface of said frame, said harness member being retained adjacent a user's leg during use; and said frame including a tibial restricting portion, said tibial restricting portion being disposed so as to extend along and substantially parallel to the medial shaft of a user's tibia and to be maintained in contact with a user's tibia placed within the brace, thereby preventing any unwanted movement or rotation of the user's tibia.

17. The leg brace of claim 16, wherein each structural member of said frame is formed with a substantially triangular cross-section.

18. The leg brace of claim 17, wherein said substantially triangular cross-sectioned frame is formed with a rigid outer thermoplastic layer of composite material, and a less dense, thermoplastic foam contained within said outer layer.

19. The leg brace of claim 16, wherein said harness member is formed with quilts formed therein.

20. The leg brace of claim 16, wherein said harness is attached to an inside surface of said frame.

21. The leg brace of claim 20, wherein said frame is formed with rivet inserts formed on the inside surface thereof, said harness further containing rivets to be inserted into said rivet inserts to retain said harness only against the surface of said frame facing the user's leg during use.

* * * * *

UNITED STATES PATENT AND TRADEMARK OFFICE
CERTIFICATE OF CORRECTION

PATENT NO. : 5,891,071
DATED : April 6, 1999
INVENTOR(S) : Jeffrey Stearns and Juan Bautista Paez It is certified that error appears in the above-indentified patent and that said Letters Patent is hereby corrected as shown below:

ON THE TITLE PAGE

Change: "Lenox Hill, a Division fo Dobi-Symplex, Bethesda, Md."

to

--[73] Assignee: Lenox Hill, a Division of Dobi-Symplex, Bethesda, Md. --

Signed and Sealed this

Thirty-first Day of August, 1999

Attest:

Q. TODD DICKINSON

*Attesting Officer*     *Acting Commissioner of Patents and Trademarks*